United States Patent [19]
Richmond

[11] Patent Number: 5,102,388
[45] Date of Patent: Apr. 7, 1992

[54] SEQUENTIAL DELIVERY SYRINGE

[76] Inventor: John E. Richmond, 22 Short Rd., Doylestown, Pa. 18901

[21] Appl. No.: 731,134

[22] Filed: Jul. 15, 1991

[51] Int. Cl.⁵ .............................. A61M 37/00
[52] U.S. Cl. ........................ 604/88; 604/191
[58] Field of Search .......... 604/82, 86, 87, 88–92, 604/191, 201, 203, 244, 416

[56] References Cited

U.S. PATENT DOCUMENTS

| | | | |
|---|---|---|---|
| 3,785,379 | 1/1974 | Cohen | 604/88 |
| 3,911,916 | 10/1975 | Stevens | 604/203 |
| 4,044,758 | 8/1907 | Patel | 604/191 |
| 4,055,177 | 10/1977 | Cohen | 604/88 |
| 4,424,057 | 1/1985 | House | 604/88 |
| 4,643,721 | 2/1987 | Brunet | 604/191 |
| 4,820,286 | 4/1989 | van der Wal | 604/191 |

FOREIGN PATENT DOCUMENTS 2210268 6/1989 United Kingdom ............... 604/191

Primary Examiner—C. Fred Rosenbaum
Assistant Examiner—Sharon Finkel
Attorney, Agent, or Firm—Charles I. Brodsky

[57] ABSTRACT

The syringe of the invention segregates various fluids or solutions within separate compartments of its barrel, to be delivered in a specific sequence as they are expelled from the delivery tip by actuation of its plunger. A plurality of stoppers are incorporated within the barrel, with all but the one adjacent to the plunger includng a piercing device to penetrate each following stopper in sequence. The length of the piercing shaft of each such device is selected sufficient to pierce the stopper advancing towards it, yet not so long as to reach the piercing shaft of that advancing stopper.

10 Claims, 2 Drawing Sheets

SEQUENTIAL DELIVERY SYRINGE

FIELD OF THE INVENTION

This invention relates to syringes, in general, and to a new and improved syringe as may be employed in the field of medicine or industry to perform functions previously performed by the use of multiple numbers of syringes.

BACKGROUND OF THE INVENTION

As is well known and understood, numerous instances exist in the field of medicine or industry where a single task is often performed following the multiple reloading of a single syringe, or the use of multiple numbers of syringes. For example, with such microsurgical instruments as forceps or scissors, a proper cleaning procedure requires various detergents, lubricants and drying agents, otherwise the instruments are inadequately maintained and subject to premature deterioration. As typically employed in microscopic eye surgery, as an illustration, the blood and other coagulants which are present infiltrate the forceps and scissors employed, and must be flushed, cleaned, and properly stored away to prevent corrosion and frequently, recurrent jamming. Even where "air" serves as the fluid or solution to be injected into the medical, or industrial, instrument for the purpose of cleansing, an adaptor must further be employed to ensure that that which is forced from the syringe correctly enters the instrument for carrying out the various "flushing" steps. Because a proper cleaning procedure typically requires various detergents, lubricants and drying agents, it then becomes necessary to repeatedly detach the operating tip of the instrument and the adaptor so that the syringe may be withdrawn and its barrel refilled with the next appropriate fluid. In many operating facilities, analysis has shown the procedure employed to be impractical, with the ensuing results being a gradual deterioration in the high degree of care necessitated by such microsurgical instruments—which many times cost in the range of $1,250.00-$1,500.00.

The obvious alternative, having readily available multiple numbers of syringes—each filled with the appropriate fluid or solution necessary—is not very practical, either, because of the high costs involved in purchasing and maintaining these syringes for use, and because it requires a properly controlled procedure of employing each individual syringe in correct sequence. There, for example, a first syringe might be employed for performing a "washing" function, a second syringe maintained to then provide a "rinse", a third syringe provided for "lubrication", and then a fourth syringe to to flush the instrument with "air" so as to blow everything throughout the working parts of the device.

On top of this—and, whether one is employing a single, refillable syringe, or a multiple number of pre-filled syringes—is the added difficulty that each time a new material is to be injected, the syringe must be removed from the instrument (or from an injection site where multiple fluids or solutions are to be injected into a patient), adding to the time for performing the procedure, or raising the obvious difficulty of having to continually find new injection sites on the body each time a new material is to be injected.

OBJECTS OF THE INVENTION

It is an object of the present invention, therefore, to provide a new and improved syringe which overcomes the limitations and disadvantages of those presently existing in the prior art.

It is another object of the invention to provide a new and improved syringe in which various fluids or solutions may be injected in a single application, whether it be in the cleansing of instruments employed in medicine or industry, or whether employed after a single injection site on a person or body has been determined.

SUMMARY OF THE INVENTION

As will become clear hereinafter, the present invention describes a syringe in which small amounts of fluids and/or solutions may be delivered in a segregated manner through the loading of its barrel in a compartmentalized fashion; and so that a single, complete advancement of its plunger dispenses all fluids and solutions in a sequential fashion. As will be seen, the syringe segregates these various fluids and solutions within defined compartments of its barrel, to be delivered in specific sequence as they are expelled from the delivery tip by actuating the plunger. A plurality of stoppers will be seen to be incorporated within the barrel, between which the various fluids and/or solutions are filled, and with all the stoppers but the one adjacent to the plunger including a piercing device to penetrate each following stopper in sequence. In accordance with the preferred embodiment described below, the length of the piercing shaft of each such device is selected sufficient to pierce the stopper advancing towards it, yet not so long as to reach the piercing shaft of that advancing stopper.

With the syringe thus being able to sequentially deliver its fluids and/or solutions in turn, it will be seen and understood that the syringe may then be pre-filled or loaded with the various detergent, rinse, lubricant and air fluids in segregated compartments, and so that once the adaptor couples the syringe to the instrument to be cleaned—or injects it into the person or body at the desired location—a single, complete thrust of the plunger then advances the various fluids through the tip of the syringe in one continuous, sequential delivery—thereby eliminating the confusion as to the proper materials or fluids to use, as well as the tedious and time-consuming manner in which their administration must be properly presented.

BRIEF DESCRIPTION OF THE DRAWINGS

These and other features of the present invention will be more clearly understood from a consideration of the following description, taken in connection with the accompanying drawing in which.

DETAILED DESCRIPTION OF THE DRAWINGS

Figure 1A:
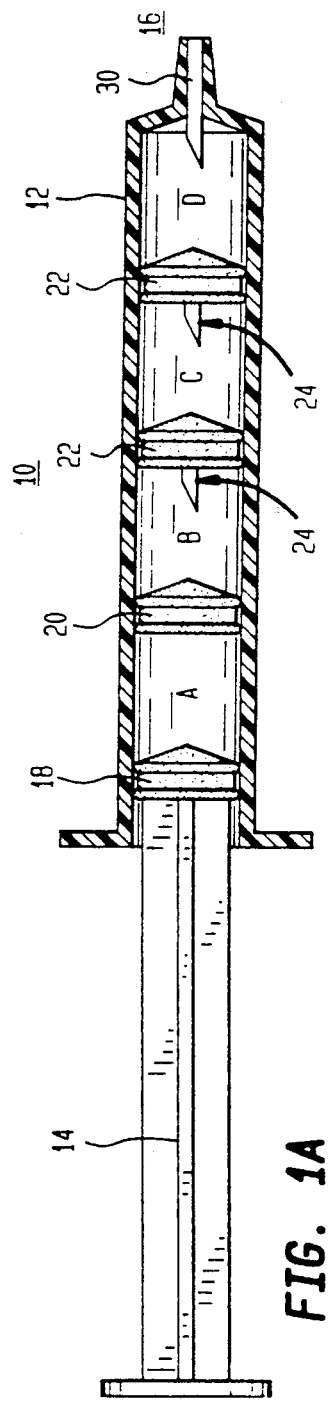
FIGS. 1a-1c illustrate a sequential delivery syringe according to a preferred embodiment of the invention and helpful in an understanding of its operation.
Figure 1B:
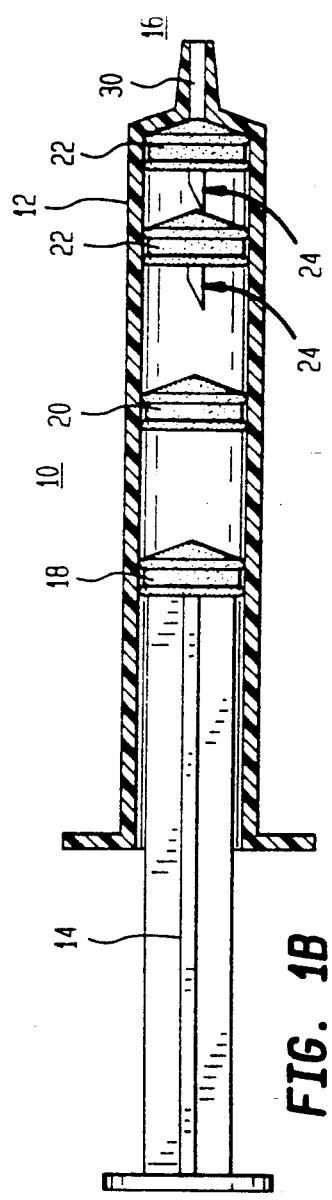
Figure 1C:
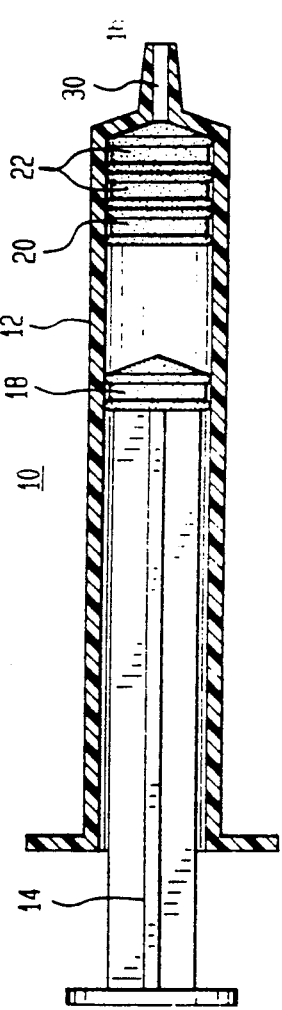
Figure 2A:
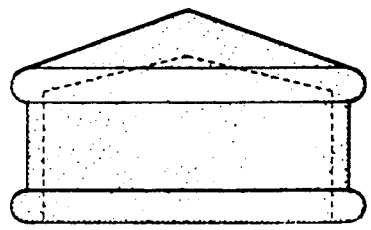
FIGS. 2a-2d are views of several of the component parts of the syringe of FIGS. 1a-1c, partially in section-form, helpful in an understanding of the sequential delivery of fluids and/or solutions.
Figure 2B:
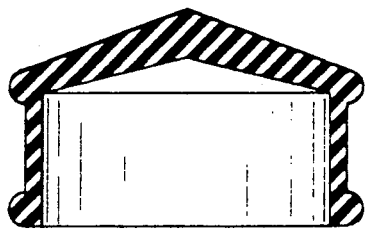
Figure 2C:
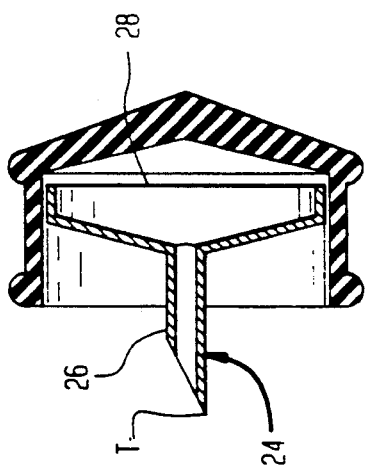

Referring to FIGS. 1a-1c, the sequential delivery syringe of the invention is illustrated by the reference numeral 10, having a barrel 12 and plunger 14, by means of which any fluids and/or solutions within the barrel 12 are forced outwardly through its delivery tip 16. To effectuate this, a "drive stopper" 18 is shown, coupled to the plunger 14 (FIGS. 1a-1c), and as reproduced in FIG. 2a as having the cross-section depicted in FIG. 2b. In accordance with the invention, the stopper 18 is preferably composed of a pliable material to create a substantially fluid-tight seal around its outer periphery.

Also shown in FIGS. 1a-1c is a second stopper 20 within the barrel 12, likewise composed of a pliable material to similarly create a substantially fluid-tight seal about its periphery, and forming a first compartment A between the stoppers 18, 20 within which any included fluid or solution becomes segregated.

Additionally, in accordance with the invention, at least one additional stopper—and, as illustrated in FIGS. 1a-1c & 2d, a pair of additional stoppers—is included, identified by the reference numeral 22. As will be appreciated, a piercing device 24 is inserted within, or otherwise affixed to, the additional stopper(s) 22 of a design and configuration to enable it to pierce the second stopper 20 or the additional stopper(s) 22 advancing towards it. Before considering this piercing device 24 and its added stopper 22 in more detail, it is first to be understood that these additional stoppers 22 also are composed of pliable materials to create, as before, substantially fluid-tight seals around their peripheries. In this manner, it will be seen that a series of added compartments B, C, D are formed, each of which may be pre-filled or loaded with a fluid, or solution of choice.

Figure 2D:
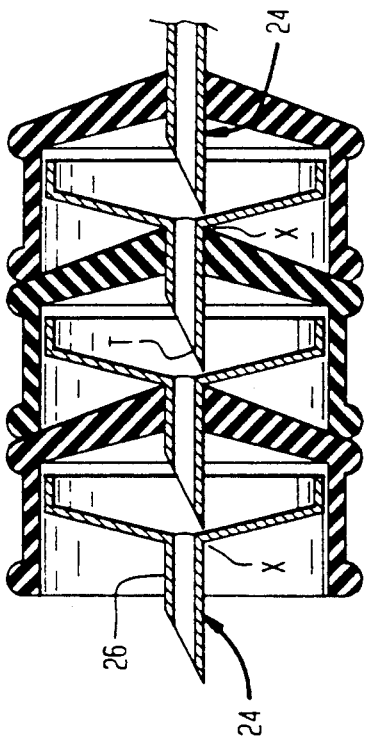

Thus, and in order to carry out the objectives of the present invention, certain other requirements will be seen to be necessary. First of all, the length of the piercing shaft is selected of a sufficient dimension to pierce the second stopper 20 or the additional stopper(s) 22 advancing towards it, but yet of such limited length as to stop short of the piercing shaft contained within the piercing device 24 in the following stopper (FIG. 2d, the tip T of the piercing shaft 26 falling short of reaching the piercing shaft point X of the stopper advancing towards it). Secondly, and in accordance with the invention, the base 28 of each piercing device 24 fits within the additional stoppers 22 so as to present a chamber into which the advancing piercing shaft 26 of the preceding piercing devices 24 enter and be contained as the various additional stoppers 22 "nest" upon one another as the plunger 14 advances (FIG. 2d).

As thus described, the arrangement of FIGS. 1a-1c will be seen to represent a syringe having four segregated compartments A-D, and with a delivery tip 16 itself containing a piercing device 30 of a type typically found in a prior-art cartridge syringe frequently used. A cap (not shown) would normally be placed over the delivery tip 16, so as to create a fluid-tight compartment when not in use, but one where the cap could be removed and an accessory tip attached for appropriate delivery of the fluid to the microsurgical instrument, to the industrial tool, or to the person or body where the fluid injection is to occur.

With such cap then in place over the delivery tip, each of the compartments A-D will be seen to be fluid-tight—and, for the cleansing of a microsurgical instrument, may include a detergent in compartment D, a rinse in compartment C, a lubricant in compartment B, and a "air" in compartment A, with each compartment being segregated one from another. But, by then removing the cap and applying pressure on the plunger 14, all the stoppers 20 and 22 will be seen to advance uniformly as the fluid in the chamber closest to the delivery tip (compartment D) is allowed to exit. With constant pressure on the plunger, then, all the fluid in compartment D will first evacuate under the force applied by the additional stopper 22 nearest the delivery tip. As the plunger 14 continues to force the second stopper 20 and its adjacent additional stopper 22 to the right, as shown in the drawings, the piercing device 30 of the delivery tip 16 punctures that first, or nearest additional stopper 22, and to the extent that the fluid, or solution, within the next chamber (compartment C) is forced through that nearest additional stopper 22 and out the piercing device 30 and delivery tip 16. (At this point, then, the first, nearest additional stopper 22 is nested at the end of the syringe, while the remaining additional stopper(s) 22 continue to advance uniformly under the force applied by the plunger 14 (FIG. 1b).)

As the plunger action continues, the piercing shaft 26 of the first additional stopper 22 then penetrates into the chamber of the second additional stopper 22, to allow the fluid or solution segregated in compartment B to flow through the piercing shafts and out the delivery tip of the syringe. As the action continues, the plunger advancement progresses until the piercing shaft 26 of the second additional stopper 22 ultimately penetrates the stopper 20, so as to create a channel by means of which the fluid and/or solution of compartment A is expelled outwardly through the delivery mechanism (FIG. 1c). Thus, by a single, continuous actuation of the plunger 14, a sequential delivery of the fluids and/or solutions in compartments D, C, B, A are expelled, without the need for any refilling or reloading of the syringe in use, and without any need for disconnecting it from the injection site or instrument being cleansed. Obviously, any desired number of additional stoppers 22 may be utilized, and any arrangements of fluids and/or solutions may be filling the various segregated compartments. In this manner, the sequential dispensing of various fluids and/or solutions can be easily controlled and maintained.

While there have been described what are considered to be preferred embodiments of the present invention, it will be readily appreciated by those skilled in the art that modifications can be made without departing from the scope of the teachings herein. Thus, while experimentation has shown that optimum results follow if the piercing shaft 26 is pointed to aid penetration, other configurations may be employed equally as well. Similarly, although described as a piercing device having a conical base, other configurations can similarly be employed—as long, however, as the piercing shaft employed is of sufficient length so as to penetrate the next sequential stopper which advances upon it, but yet not so long as to abut against the advancing shaft. And, whereas the invention may be interpreted as requiring the individual filling, or loading of the compartments A through D for use, it will be seen equally as apparent that a pre-filled cartridge arrangement can be inserted into the barrel, so as to be acted upon by the drive stopper 18, with the cartridge then inserted having the individual compartments and piercing devices as illustrated in FIGS. 1 and 2. As long as the piercing devices are arranged so that their shafts face the advancing stoppers, the sequential evacuation of the chamber fluids and solutions will follow, with the drive stopper 18 then expelling the fluid or solution from the last remaining compartment, to eventually nest amongst the other stoppers 20, 22 at the delivery end of the barrel 12. For at least such reasons, therefore, resort should be had to the claims appended hereto for a true understanding of the scope of the invention.

I claim:

1. A syringe comprising:
   a barrel, having a delivery end;
   a plunger;
   a first stopper coupled to said plunger and inserted within said barrel;
   a second stopper inserted within said barrel, positioned between said first stopper and the delivery end of said barrel; and
   at least two additional stoppers inserted within said barrel, positioned between the delivery end of said barrel and said second stopper, each being coupled with a piercing device having a piercing shaft facing in the direction of said second stopper, and with each piercing shaft being of sufficient length to pierce the stopper advancing towards it upon actuation by said plunger.

2. The syringe of claim 1 wherein said delivery end of said barrel also includes a piercing device facing in the direction of said additional stopper(s).

3. The syringe of claim 1 wherein the piercing shaft of each piercing device is also selected of a length insufficient to reach the piercing shaft of that piercing device coupled with the stopper nearest advancing towards it.

4. The syringe of claim 3 wherein each of said first, second and said additional of stoppers are composed of a pliable material to create substantially fluid-tight seals around the outer peripheries thereof.

5. The syringe of claim 4 wherein individual ones of a plurality of fluids and solutions are included between adjacent stoppers within said barrel.

6. A syringe comprising:
   a barrel, having a delivery end;
   a plunger;
   a first stopper coupled to said plunger and inserted within said barrel;
   a second stopper inserted within said barrel, positioned between said first stopper and the delivery end of said barrel;
   a third stopper inserted within said barrel, positioned between said second stopper and the delivery end of said barrel; and
   a piercing device coupled with said third stopper, having a piercing shaft facing in the direction of said second stopper; and
   with said shaft being of sufficient length to pierce said second stopper when said plunger is actuated to advance said first stopper towards said second stopper;
   a fourth stopper inserted within said barrel, positioned between the delivery end of said barrel and said third stopper, and being coupled with a piercing device having a piercing shaft facing in the direction of said third stopper, and with the piercing shaft coupled with said forth stopper being of sufficient length to pierce said third stopper advancing towards it upon actuation by said plunger.

7. The syringe of claim 6 wherein said delivery end of said barrel also includes a piercing device facing in the direction of said fourth stopper.

8. The syringe of claim 6 wherein the piercing shaft of said piercing device coupled to said fourth stopper is also selected of a length insufficient to reach the piercing shaft of said third stopper, and wherein the piercing shaft of said piercing device coupled to said third stopper is also selected of a length insufficient to reach the piercing shaft of said second stopper.

9. The syringe of claim 8 wherein each of said first, second, third and fourth stoppers are composed of a pliable material to create substantially fluid-type seals around the outer peripheries thereof.

10. The syringe of claim 9 wherein individual ones of a plurality of fluids and solutions are included between adjacent stoppers within said barrel.

* * * * *